United States Patent [19]

Salib

[11] Patent Number: 4,722,686
[45] Date of Patent: Feb. 2, 1988

[54] SURVEYING INSTRUMENT AND METHOD FOR DUAL-PATH INSERTION DENTURES

[75] Inventor: M. Michael Salib, Inverness, Ill.

[73] Assignee: Northwestern University, Evanston, Ill.

[21] Appl. No.: 877,347

[22] Filed: Jun. 23, 1986

[51] Int. Cl.$^4$ ............................................. A61C 19/04
[52] U.S. Cl. ....................................... 433/72; 433/75; 433/49
[58] Field of Search ....................... 433/72, 75, 76, 56, 433/53, 74, 49, 50, 51

[56] References Cited

U.S. PATENT DOCUMENTS

| | | | |
|---|---|---|---|
| 2,528,053 | 10/1950 | Harris | 433/75 |
| 3,417,471 | 12/1968 | Mitchell | 433/72 |
| 4,573,917 | 3/1986 | Erickson | 433/72 |

FOREIGN PATENT DOCUMENTS 0486657  9/1952  Canada .................................. 433/72

Primary Examiner—Gene Mancene
Assistant Examiner—Adriene J. Lepiane
Attorney, Agent, or Firm—Tilton, Fallon, Lungmus

[57] ABSTRACT

An instrument and method for establishing those relationships and modifications required for making and properly fitting a removable partial denture suitable for dual paths of insertion and removal. The instrument includes a platform having a surface for supporting a dental model and, alongside that surface, at least one guide track. An upstanding base is supported upon the track for movement therealong and is equipped with an extendable and rotatable head. The head carries a pivot shaft that is parallel with the plane of the support surface and that may be adjusted longitudinally along, and rotated about, its longitudinal axis. In use, such axis is aligned with that point on an abutment tooth of the model that is to serve as the intended point of rotation for insertion and removal of a partial denture. A transverse bar is carried by the shaft and is equipped at its end with a blade parallel with the axis of the shaft. By extending the bar to bring the blade into contact points for the respective abutment teeth, and then rotating the pivot shaft about its axis, a user may readily and accurately establish the interference areas requiring removal of tooth material and, in addition, those areas where wax must be added (and may later be trimmed by the blade) to block out undercuts that would otherwise prevent proper insertion and removal of the denture.

11 Claims, 5 Drawing Figures

SURVEYING INSTRUMENT AND METHOD FOR DUAL-PATH INSERTION DENTURES

BACKGROUND AND SUMMARY

The concept of dual path of insertion has been applied to removable partial dentures for many years, as brought out by King, G. E., *Dual-Path Design for Removable Partial Dentures*, Journal of Prosthetic Dentistry, Vol. 39, No. 4, pp. 392-395 (April 1978). In the dual-path system, the first path, or approach of the metal framework of the denture to the natural teeth, is a maneuver to gain access to undercuts otherwise inaccessible from a single path of insertion. As soon as the framework has gained access to those desired undercuts, it is then rotated into a fully seated position, such rotation constituting the second and final path of insertion. Removal requires the reverse sequence of steps. Since reverse rotation of the denture must precede its removal from the undercut areas, the undercuts effectively lock the denture in place until removal is desired.

Although dentures designed to utilize the so-called "dual-path insertion" are advantageous in many respects, their popularity has been limited to some extent by the difficulty in establishing precisely those areas where tooth structure must be altered slightly to prevent interference, or where wax should be added and trimmed on a dental model (e.g., a master cast) to prevent interferences to rotational movement for the framework of the completed denture. Precision is required in ascertaining and avoiding undesired interferences, but instrumentation necessary for making such determinations has been lacking and, in general, removable partial dentures of the dual-path type have required that dental work be performed largely on a trial-and-error basis.

Instrumentation for other types of denture work are well known as revealed, for example, by U.S. Pat. Nos. 4,007,531, 2,108,980 2,528,053, 2,618,068, 2,910,773, 4,196,519, and 1,216,596. Other patents of general interest are U.S. Pat. Nos. 4,457,714, 4,474,499, 4,481,162, and 2,676,407.

An important aspect of this invention therefore lies in providing a surveying instrument, and its method of use, for establishing those relationships and modifications required for making and precisely fitting a removable partial denture utilizing the dual-path concept. The instrument includes a platform having a planar surface on which a dental model may be secured affixed. The platform includes track means which preferably takes the form of two tracks, parallel with each other and with the saggital plane of the model. A base member is adapted to be mounted for longitudinal movement upon each of the tracks and is equipped with locking means to secure it in a desired position of adjustment. The upstanding base has an upwardly-facing socket that carries a cylindrical head, the head being both rotatable and vertically extendable. A pivot shaft is mounted upon the head with its longitudinal axis extending along the plane of the support surface for the dental model, and a blade-support bar extends through a transverse opening at the tip of the bar for supporting a blade that extends along a line parallel with the longitudinal axis of the pivot shaft. Locking means are provided for securing the blade-support bar and the rotatable head in selected positions of adjustment. By aligning the tip of the shaft with the intended point of rotation (on the dental model) for insertion and removal of a partial denture, the blade-support bar may be extended and retracted to bring the blade into contact with the model's abutment teeth, and the pivot shaft may then be rotated to shift the blade along concentric arcs to establish clearances and to reveal areas where tooth material should be removed, supplemented, or trimmed, to achieve a correct and operative path of insertion and removal for a partial denture of the dual-path type.

Other features, advantages, and objects of the invention will become apparent from the specification and drawings.

DRAWINGS

DETAILED DESCRIPTION OF PREFERRED EMBODIMENT

Figure 1:
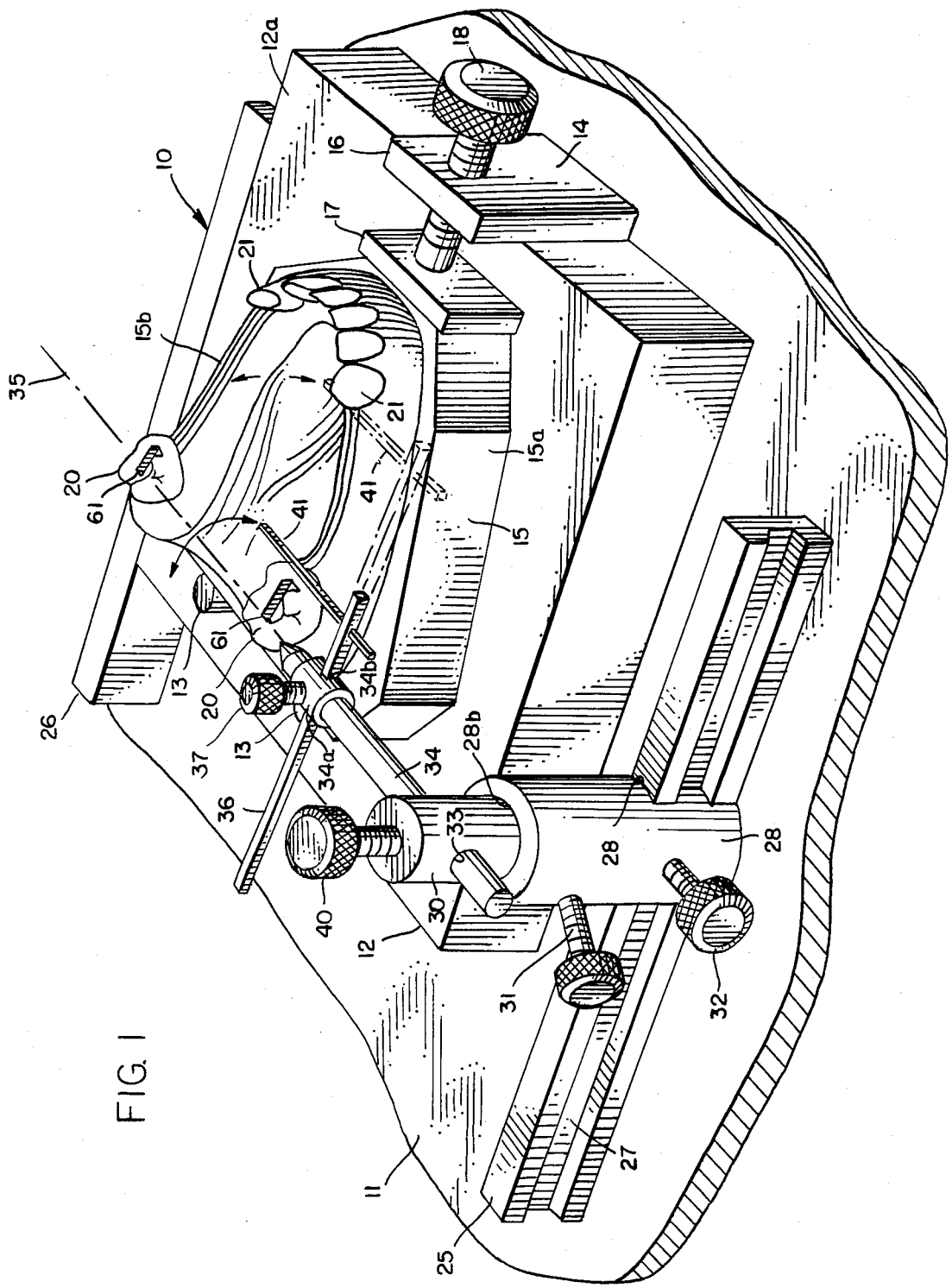
FIG. 1 is a perspective view of a surveying instrument embodying the present invention, the instrument being shown with a dental model supported on the platform.
Figure 2:
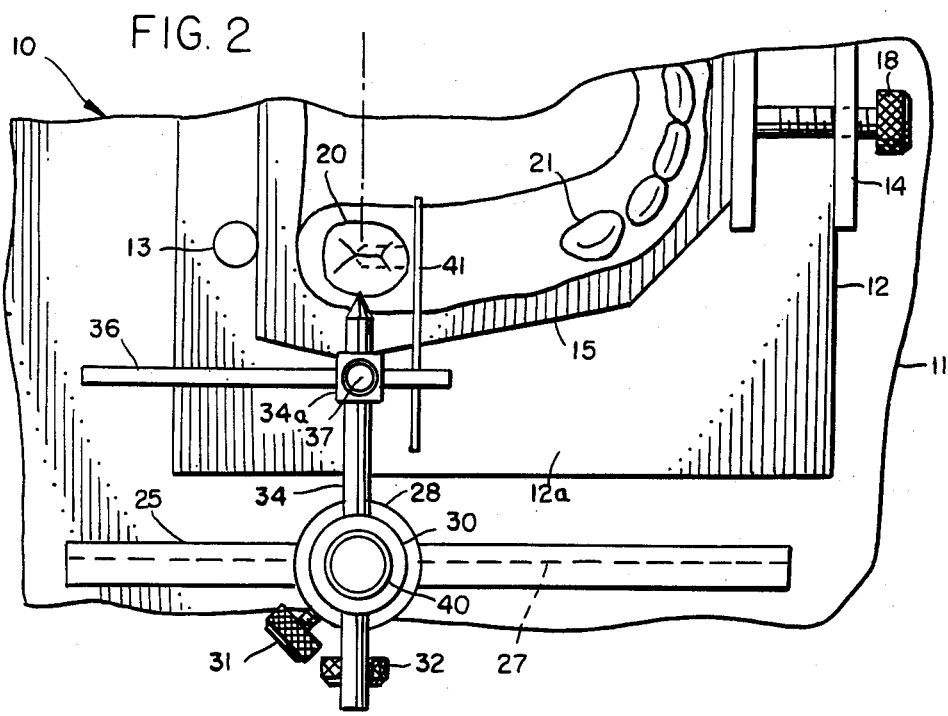
FIG. 2 is a fragmentary top plan view of the instrument.

Referring to FIGS. 1 and 2, the numeral 10 generally designates a surveyor having a horizontal platform 11 having an elevated rectangular portion 12 with a planar top surface 12a. A plurality of upstanding posts 13, along with anchoring means in the form of a clamp 14, function to hold a dental model 15 in position on support surface 12a. The clamp includes a fixed plate 16, a movable plate 17, and a knob-equipped screw 18, but other means for anchoring the model in position may be provided.

The dental model, or denture model, is conventional and includes a mounting plate portion 15a and an integral cast 15b of the tooth structure of one of a patient's jaws for which a removable partial denture is to be made. The model or cast is ordinarily formed of plaster, but other materials may be used. In the model depicted for illustrative purposes in FIG. 1, a number of mandibular posterior teeth are absent but abutment teeth in the form of molars 20 and eyeteeth 21 remain. The term "abutment" is used here to mean those teeth to which the metal frame of the removal partial denture is to be attached or supported.

Alongside the raised portion 12 of platform 11 are a pair of tracks 25 and 26. The two tracks are parallel to each other and to the saggital plane of the dental model, and are identical in construction. Each track is straight and has an outwardly-facing longitudinal channel 27. A base member 28 is recessed at 28a to receive each track for guided movement therealong. Two such base members, one for each track, may be provided but, in the construction shown, a single base member is provided and may be shifted from one track to the other as needed.

The base member is generally cylindrical in shape and is provided with an upwardly-facing socket 28b for receiving a rotatable and extendable head 30. In the illustration given, the head is generally cylindrical in shape with its lower portion received in socket 28b. The head may be rotated about its vertical longitudinal axis and may also be raised or lowered along that axis and, when a desired position has been selected, may be locked in that position by locking means in the form of a knob-equipped screw 31 that extends through the wall of the base member and engages the side surface of the rotatable head 30. Similar locking means 32 extends through the lower wall portion of member 28 and engages the track 25 within channel 27 to hold the base member at any selected position along the length of the track.

The rotatable head 30 has a transverse horizontal bore 33 that receives one end of a straight, elongated, cylindrical pivot shaft 34. It will be noted from FIG. 1 that the longitudinal axis 35 of that shaft extends along a plane parallel with support surface 12a. The opposite end or tip portion 34a of the pivot shaft may be enlarged and an opening 34b extends transversely through the tip portion and slidably receives an elongated bar 36. Locking means in the form of a knob-equipped screw 37 extends through the wall of the shaft into opening 35 for engaging the bar 36 and holding it in a selected position of adjustment. It will be observed that the bar is of non-circular cross section (preferably rectangular) so that while it is free to slide longitudinally through the opening of the pivot shaft (when screw 37 is retracted), it cannot be rotated in that opening.

A similar knob-equipped screw 40 may be provided at the upper end of head 30 for engaging pivot shaft 34 on those occasions where movement of the pivot shaft is to be restrained. Ordinarily, pivot shaft 34 is not locked against pivotal and longitudinal movement, but there may be occasions when some limited frictional resistance to free movement of the pivot shaft is desirable, in which case screw 40 may be used to provide the necessary braking effect.

The extreme tip of pivot shaft 34 may be pointed, as shown clearly in FIGS. 1 and 2. Such tapering or pointing facilitates proper positioning of the shaft when its axis 34 is to be aligned with the intended point of rotation of a removable partial denture, as will be described in greater detail hereinafter.

The extendable/retractable bar 36 is equipped at one end with a straight, narrow blade or probe 41 that extends in a direction parallel with axis 35 of the pivot shaft 34. The blade may be formed of hardened steel or other suitable material and functions both as a cutting or trimming device and as an indicator or gauge. For cutting purposes, the blade's lower edge (also, if desired, its upper edge) may be sharpened. Since bar 36 is slidable transversely through pivot shaft 34, the blade may be shifted, when screw 37 is loosened, between the solid-line and broken-line positions shown in FIG. 1.

Figure 5:
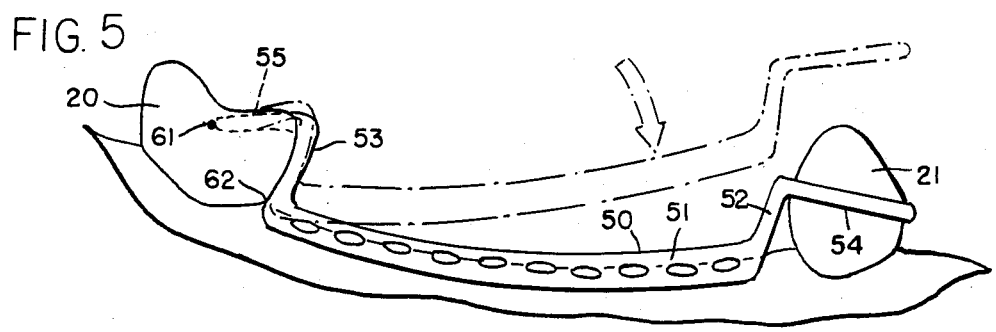
FIG. 5 is a side elevational view illustrating the positioning of a removal denture of the dual-path type.

FIG. 5 illustrates one side of a removable partial denture designed for dual-path insertion and removal. Only the metal framework of the denture is shown. The denture frame 50 includes meshwork 51 which fits over the "saddle" portion between attachment or abutment teeth 20 and 21, the meshwork serving as a base for mounting the artificial teeth, and also includes a mesial proximal plate 52, a distal or posterior proximal plate 53, a clasp or clip 54 for engaging opposite sides of the mesial abutment tooth 21, and an occlusal rest 55 extending distally from proximal plate 53. Since such structure is well known and does not constitute any part of the instrument of this invention, a description and further detail is believed unnecessary. It is to be understood, however, that FIG. 5 illustrates something less than one half of the metalwork of the removable partial denture and that another similar section is connected by a lingual bar to the section shown and would engage the saddle along the opposite side of the patient's jaw (not shown).

Figure 4:
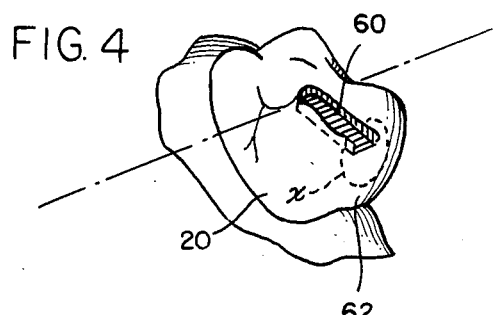
FIG. 4 is a fragmentary perspective view of a molar illustrating its undercut mesial surface, the recess for the occlusal rest, and an area of interference requiring removal of tooth material.

FIG. 4 shows a molar 20 having a portion of its crown removed to provide a depression or seat 60 for the occlusal rest 55 of partial denture 50. To insert such a denture, the tip of the occlusal rest 55 is inserted into the seat until it engages the distal shoulder of that seat. Thereafter, the mesial end of the denture is pivoted downwardly about the pivot point or line 61 of contact between the tip of the occlusal rest 55 and the distal shoulder of the seat. Such downward rotation is continued until the clips 54 engage abutment teeth 21. When the denture is fully lowered, as shown in solid lines in FIG. 5, the undercut 62 of the mesially-inclined molar 20 is engaged by proximal plate 53 to prevent upward lifting movement of plate 53 and occlusal rest 55.

It is important that the heel of proximal plate 53 engage undercut 62 to block occlusal displacement of the denture, but it is also essential that there be no interference by tooth 20 that would prevent the heel portion from gaining access to the undercut during gingival rotation of the framework. Thus, in FIG. 3 the shaded portion "x" represents that portion on the mesial side of tooth 20 that would interfere with rotation of the denture frame into a fully seated position. In the illustration given, some of the enamel in area x must be removed to eliminate such interference (see also FIG. 4). One function of the surveyor 10 is to ascertain the extent and location of tooth material that must be removed to avoid interference.

In use of the surveying instrument, the technician aligns the axis 35 with the distal ends of the occlusal seats formed in the crowns of teeth 20. Such axis should pass through the pivot point 61 of at least one of the teeth 20, and preferably through the pivot points of both teeth. Bar 36 is then adjusted, and pivot shaft 34 is rotated, until blade contacts the mesial undercut 62 which is to serve as the distal retention means for the denture. If blade 41 can be pivoted upwardly about the axis 35 of shaft 34 without obstruction along the mesial surface of tooth 20, then no further removal of the material of tooth 20 is necessary to avoid interference by that tooth. However, in the illustration of FIG. 3, the mesial protrusion or contour of tooth 20 in zone x constitues an interference that would prevent proper rotation of the removal of partial denture frame into fully seated position. Removal of tooth material in zone x is therefore indicated.

Blade 41 may be used to achieve such removal from the plaster dental model or, alternatively, suitable filing or grinding procedures may be employed. When the correct amount of material has been trimmed away, blade 41 will just clear the mesial surface of tooth 20 as it sweeps downwardly into undercut 62.

Figure 3:
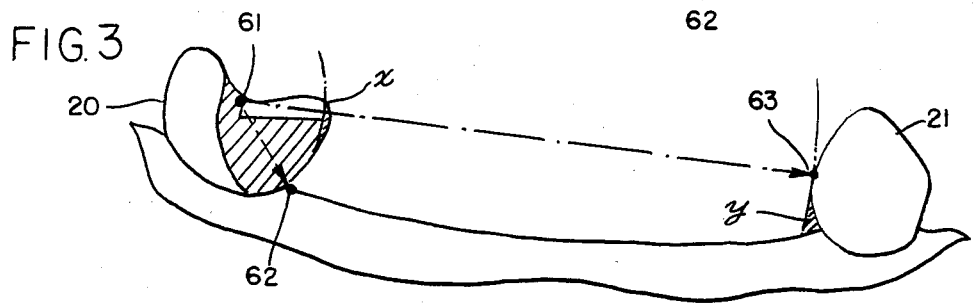
FIG. 3 is a diagramatic side elevational view illustrating the action of the surveying instrument in revealing clearances and establishing areas of interference to be eliminated in making and fitting a denture of the dual-insertion type.

Following removal of the interference presented by tooth 20, knob 37 is loosened and bar 36 is extended to shift blade 41 into the broken line position shown in FIG. 1. More specifically, the blade is shifted mesially until it just touches that surface of abutment tooth 21 closest to the axis 35 of the pivot shaft 34 (or closest to pivot point 61, as shown in FIG. 3). That point is designated by numeral 63 in FIG. 3. Thereafter, the blade is lowered to reveal whether an undercut exists. In FIG. 3, an undercut represented by letter "y" is located below point 63. The technician therefore fills area y with wax (or other suitable material) and lowers blade 41 to trim away excess material. The gusset of wax permits final casting of the denture metalwork without risk that interference will occur at point 63 to prevent rotation of the final denture into its seated and anchored position.

These procedures are then repeated with the base member 28 removed from track 27 and fitted onto track 26. As already indicated, such repositioning may be eliminated, and the various procedural steps may be expedited, if duplicate assemblies (i.e., base member 28, head 30, pivot shaft 34, bar 36, and blade 41) were provided on opposite sides of the dental model, one carried by each of the tracks 26 and 27.

While in the foregoing I have disclosed the instrument and method of this invention in considerable detail for purposes of illustration, it will be understood by those skilled in the art that many of these details may be varied without departing from the spirit and scope of the invention.

I claim:

1. A dental surveyor for establishing those relationships and modifications required for making and properly fitting a removable partial denture suitable for dual-path insertion, comprising a platform having a planar support surface for supporting a dental model; anchoring means for securing the model in fixed position on said support surface; a guide track along said said platform adjacent to said support surface; a base member movable along said track and equipped with locking means for securing said member in any selected position therealong; a rotatable head mounted upon said base member for rotational movement about, and for longitudinal movement along, an axis normal to the plane of said support surface; locking means for releasably locking said head against movement relative to said base member; a straight, elongated pivotal shaft carried by said head, said pivot shaft having its longitudinal axis parallel with the plane of said support surface and being mounted upon said head for longitudinal movement along, and rotational movement about, said longitudinal axis; locking means for releasably locking said pivot shaft against longitudinal and rotational movement relative to said head; said shaft including a tip portion having a transverse opening therethrough; a blade-support bar slidably received in said opening of said tip portion; locking means for releasably locking said blade-support bar against movement relative to said pivot shaft; and a thin, straight blade secured to one end of said bar and extending along a line parallel with said pivot shaft; whereby, when said tip portion of said pivot shaft is aligned with an intended point of rotation, on a dental model supported upon said surface, for insertion and removal of a partial denture, said blade-support bar may be shifted to bring said blade into contact with the model's abutment teeth for said partial denture, and said pivot shaft may then be rotated to shift said blade along arcs for establishing clearance, indicating adequacy or revealing areas where tooth material should be removed, and indicating where wax should be added and trimmed, to achieve a correct path of insertion and removal of a partial denture of the dual-path type.

2. The surveyor of claim 1 in which said guide track is linear.

3. The surveyor of claim 2 in which a pair of said guide tracks are disposed on opposite sides of said support surface; said guide tracks being parallel to each other.

4. The surveyor of claim 3 in which said base member is removable from and attachable to each of said guide tracks.

5. The surveyor of claim 1 in which said blade-support bar is non-circular in cross section.

6. The surveyor of claim 5 in which said blade-support bar is rectangular in cross section.

7. The surveyor of claim 1 in which said tip portion of said pivot shaft has a pointed end.

8. The surveyor of claim 1 in which each of said locking means comprises a threaded shaft equipped with an adjustment knob for rotating such shaft into locking and unlocking positions.

9. A method for establishing relationships and modifications necessary for making and properly fitting a removable partial denture suitable for dual-path insertion and removal, comprising the steps of supporting a dental model on a support surface, said model comprising a cast of a patient's teeth and gums with the distal and mesial abutment teeth represented as they exist in the patient's jaw; aligning a pivot shaft with a point on one of said abutment teeth which is to constitute the pivot point for the occlusal rest of a first proximal plate of a removable partial denture; said pivot shaft being equipped with an extendable and retractable transverse bar having a blade at one end thereof parallel with said shaft; adjusting said bar and shaft to position said blade at the undercut of said one of said teeth; and pivoting said shaft so that movement of said blade reveals adequacy or interference portions of said one abutment tooth requiring removal.

10. The method of claim 9 including the step of extending said bar to position said blade in contact with that portion nearest said pivot shaft of the other of said abutment teeth; again pivoting said shaft to move said blade in relation to said other abutment tooth to reveal areas where wax may be added to block out undesirable undercuts for the fabrication of a removable partial denture suitable for dual paths of insertion and removal.

11. The method of claim 10 including the steps of adding wax to the undercut area of said other abutment tooth; and thereafter pivoting said shaft to shift said blade into contact with said wax to trim excessive wax from said undercut area.

* * * * *